United States Patent
Reddy

(10) Patent No.: US 6,979,325 B2
(45) Date of Patent: Dec. 27, 2005

(54) POST CIRCUMCISION DIAPER

(76) Inventor: Usha P. Reddy, 5605 Kugler Mill Rd., Cincinnati, OH (US) 45236

( * ) Notice: Subject to any disclaimer, the term of this patent is extended or adjusted under 35 U.S.C. 154(b) by 0 days.

(21) Appl. No.: 10/787,752

(22) Filed: Feb. 27, 2004

(65) Prior Publication Data

US 2005/0192551 A1    Sep. 1, 2005

(51) Int. Cl.[7] ............................. A61F 13/20; A61F 13/00
(52) U.S. Cl. ............................. 604/385.19; 604/385.09; 604/361; 128/891; 602/67
(58) Field of Search ............................. 604/385.09, 385.19, 604/385.31, 361, 346–353, 355; 128/842, 128/891; 602/67–73; D24/124, 125, 126; D2/700, 711, 712

(56) References Cited

U.S. PATENT DOCUMENTS

| | | | |
|---|---|---|---|
| 297,274 A | | 4/1884 | Levy |
| 3,212,500 A | | 10/1965 | Bardy |
| 3,316,911 A | | 5/1967 | Barr |
| 3,517,666 A | * | 6/1970 | Atlee ............................. 602/68 |
| 3,858,584 A | * | 1/1975 | Johnson ............................. 604/351 |
| 4,500,316 A | | 2/1985 | Damico |
| 4,731,063 A | * | 3/1988 | Newkirk ............................. 604/347 |
| 4,759,355 A | * | 7/1988 | Thrower ............................. 602/67 |
| 4,790,835 A | | 12/1988 | Elias |
| 4,967,768 A | * | 11/1990 | Tatro ............................. 128/891 |
| 5,009,649 A | * | 4/1991 | Goulter et al. ............................. 604/351 |
| 5,074,853 A | | 12/1991 | Bryant |
| 5,157,793 A | * | 10/1992 | Michels ............................. 2/403 |
| 5,274,854 A | * | 1/1994 | Wenner et al. ............................. 2/403 |
| D353,933 S | * | 1/1995 | Michels ............................. D2/712 |
| 5,390,376 A | * | 2/1995 | Marx et al. ............................. 2/406 |
| 5,558,659 A | | 9/1996 | Sherrod et al. |
| 5,598,587 A | * | 2/1997 | Wada ............................. 2/403 |
| 5,618,279 A | | 4/1997 | Pudlo |
| 5,702,381 A | | 12/1997 | Cottenden |
| 5,716,350 A | | 2/1998 | Ryan |
| 5,797,401 A | * | 8/1998 | Knight ............................. 128/842 |
| 5,807,299 A | * | 9/1998 | McRoberts et al. ............................. 602/67 |
| 5,810,799 A | * | 9/1998 | Slater ............................. 604/385.09 |
| 5,819,799 A | | 10/1998 | O'Dell |
| 5,989,567 A | * | 11/1999 | Dolisi ............................. 424/400 |
| 6,068,607 A | * | 5/2000 | Palmer et al. ............................. 602/67 |
| 6,245,036 B1 | * | 6/2001 | McRoberts et al. ............................. 602/67 |
| 6,307,118 B1 | * | 10/2001 | Reich ............................. 602/42 |
| 6,394,988 B1 | * | 5/2002 | Hashimoto ............................. 604/355 |
| 6,565,545 B1 | * | 5/2003 | Frenche ............................. 604/349 |
| 6,580,011 B1 | | 6/2003 | Jennings-Spring |
| 2003/0028161 A1 | | 2/2003 | Carballo |
| 2004/0107481 A1 | * | 6/2004 | Mortell et al. ............................. 2/400 |

FOREIGN PATENT DOCUMENTS

| | | | | |
|---|---|---|---|---|
| GB | 2 371 755 A | * | 8/2005 | ............. A61F 13/00 |
| WO | WO 98/43588 A1 | * | 10/1998 | ............. A61F 13/15 |

* cited by examiner

Primary Examiner—Tatyana Zalukaeva
Assistant Examiner—Michael G. Bogart
(74) Attorney, Agent, or Firm—Richard C. Litman

(57) ABSTRACT

The post circumcision diaper has an integrated protective cup situated between the outer fluid-impervious and inner absorbent layers of the diaper's front portion. The protective cup is constructed of plastic and forms an area of the diaper that is convex outward and concave inward to protect the penis of a recently circumcised baby boy from both direct and incidental pressure. In an alternative embodiment, the post circumcision diaper is formed from a protective cup that is configured for aftermarket attachment to the inside of a commercially available disposable or cloth diaper. In this embodiment, the protective cup has adhesive on its outer surface and a layer of absorbent material on its inner surface.

12 Claims, 6 Drawing Sheets

POST CIRCUMCISION DIAPER

BACKGROUND OF THE INVENTION

1. Field of the Invention

The present invention relates to disposable diapers, and more particularly to a disposable diaper with an integrated protective cup for use on a recently circumcised baby boy to minimize direct and incidental pressure on the baby's penis.

2. Description of the Related Art

Contemporary medicine has recognized the need for pain management for infants and young children who are yet unable to communicate. In particular, the need for pain management is now widely recognized for baby boys undergoing a circumcision, a procedure performed on approximately 80% of all baby boys. Yet, despite the pain and tenderness associated with circumcision, disposable diapers used on post circumcision baby boys do not protect against direct or incidental pressure on the surgical site, namely, the circumcised penis. Instead, these diapers lie directly over the surgical site, thereby causing undue irritation, pressure, and ultimately increased pain levels. Thus, a need exists for a post circumcision diaper that does not lie directly over the surgical site, but that does protect the surgical site from incidental contact.

U.S. Pat. No. 3,858,584, issued on Jan. 7, 1975 to A. M. Johnson, teaches a diaper for a male baby that has a detachable urine absorbing container and an opening through which the baby's penis is positioned prior to insertion into the container. However, because the baby's penis must be inserted through a hole in the diaper, use of the device is needlessly complex. Additionally, with the detachable urine container, the device is expensive to manufacture relative to traditional disposable diapers.

U.S. Pat. No. 4,500,316, issued on Feb. 19, 1985 to J. A. Damico, describes a disposable garment for use as an incontinence brief. Although the device bears some resemblance to the present invention, it is not useful for protecting a baby boy's penis from incidental contact, nor does it avoid direct contact with the penis.

U.S. Pat. No. 4,790,835, issued on Dec. 13, 1988 to B. Elias, discloses a urinary male diaper that is tubular in shape to fit directly onto a male penis. Although the device addresses problems associated with involuntary urinary discharge, it is not useful as a post circumcision diaper for baby boys.

U.S. Pat. No. 6,580,011, issued on Jun. 17, 2003 to B. Jennings-Spring, shows a circumcision/penile dressing that fits on the distal end of a penis for hygienic purposes. However, because the device essentially is a sleeve bandage, it is not useful as a diaper.

Other patents teaching incontinence diapers include U.S. Pat. No. 5,074,853 issued on Dec. 24, 1991 to T. L. Bryant (male incontinence diaper); U.S. Pat. No. 5,558,659 issued on Sep. 24, 1996 to E. H. Sherrod et al. (incontinence article for males); U.S. Pat. No. 5,702,381 issued on Dec. 30, 1997 to A. M. Cottenden (male incontinence device); U.S. Pat. Nos. 5,618,279 and 5,716,350 issued on Apr. 8, 1997 and Feb. 10, 1998, respectively, to R. T. Ryan (medical protection device for males); and U.S. Pat. No. 5,810,799 issued on Sep. 22, 1998 to E. Slater (diaper for a male wearer).

Additionally, U.S. Pat. No. 297,274 issued on Apr. 22, 1884 to C. H. Levy (catamenial sack); U.S. Pat. No. 3,212,500 issued on Apr. 24, 1963 to O. A. Bardy (hygienic receptacle for undergarments); U.S. Pat. No. 3,316,911 issued on May 20, 1964 to L. D. Barr (infant garment); and U.S. Pat. Publication No. 2003/0028161, published on Feb. 6, 2003 (non-intrusive urine collection apparatus) teach devices that are not useful as a diaper.

Consequently, none of the above inventions and patents, taken either singly or in combination, is seen to describe the instant invention as claimed. Therefore, a post circumcision diaper solving the aforementioned problems is desired.

SUMMARY OF THE INVENTION

The post circumcision diaper is configured to protect the penis of a recently circumcised baby boy from both direct and incidental pressure. The post circumcision diaper includes an integrated protective cup situated between the outer fluid-impervious and inner absorbent layers of the diaper's front portion. The protective cup is constructed of plastic and forms an area of the diaper that is convex outward and concave inward. When a baby boy wears the diaper, the protective cup and the concave area are positioned over the baby's penis or the baby's penis and scrotum, thereby protecting the penis or penis and scrotum against direct pressure from the diaper and incidental pressure from persons holding the baby.

In an alternative embodiment, the post circumcision diaper is comprised of a protective cup that is configured for aftermarket attachment to the inside of a commercially available disposable or cloth diaper. In this embodiment, the protective cup has adhesive on its outer surface and a layer of absorbent material on its inner surface. Additionally, the protective cup may be porous or perforated to fully use the absorptive capacity of the diaper by allowing the baby's urine to pass through the cup and into the diaper.

By protecting a baby boy's recently circumcised penis from direct and incidental pressure, the post circumcision diaper of the present invention helps prevent rubbing and irritation of the surgical site and thereby helps prevent infections that can lead to complications—requiring further surgery or an imperfect cosmetic appearance.

Accordingly, it is a principal object of the invention to provide a post circumcision diaper that prevents painful irritation and pressure on the surgical site of a recently circumcised baby boy.

It is another object of the invention to provide a post circumcision diaper that protects the surgical site of a recently circumcised baby boy from incidental pressure while an adult is holding the baby.

Still another object of the invention is to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
FIG. 1 is an environmental, perspective view of a post circumcision diaper according to the present invention as worn by a baby boy lying on his back.

The present invention is a post circumcision diaper, designated generally as 10 in the drawings, that is configured to protect the penis of a recently circumcised baby boy from both direct and incidental pressure.

Figure 3:
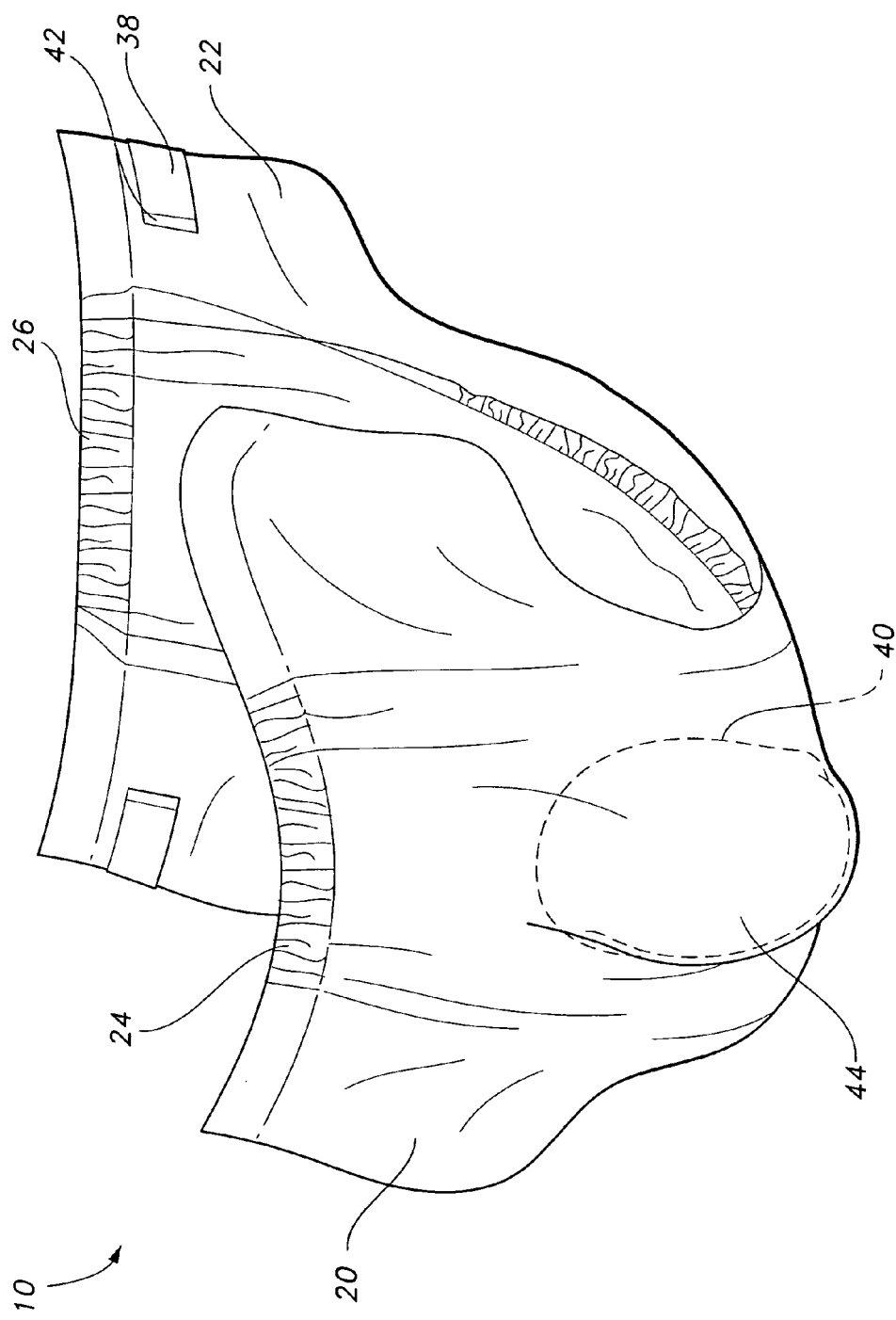
FIG. 3 is a perspective view of the post circumcision diaper, the protective cup being shown in phantom.
Figure 4:
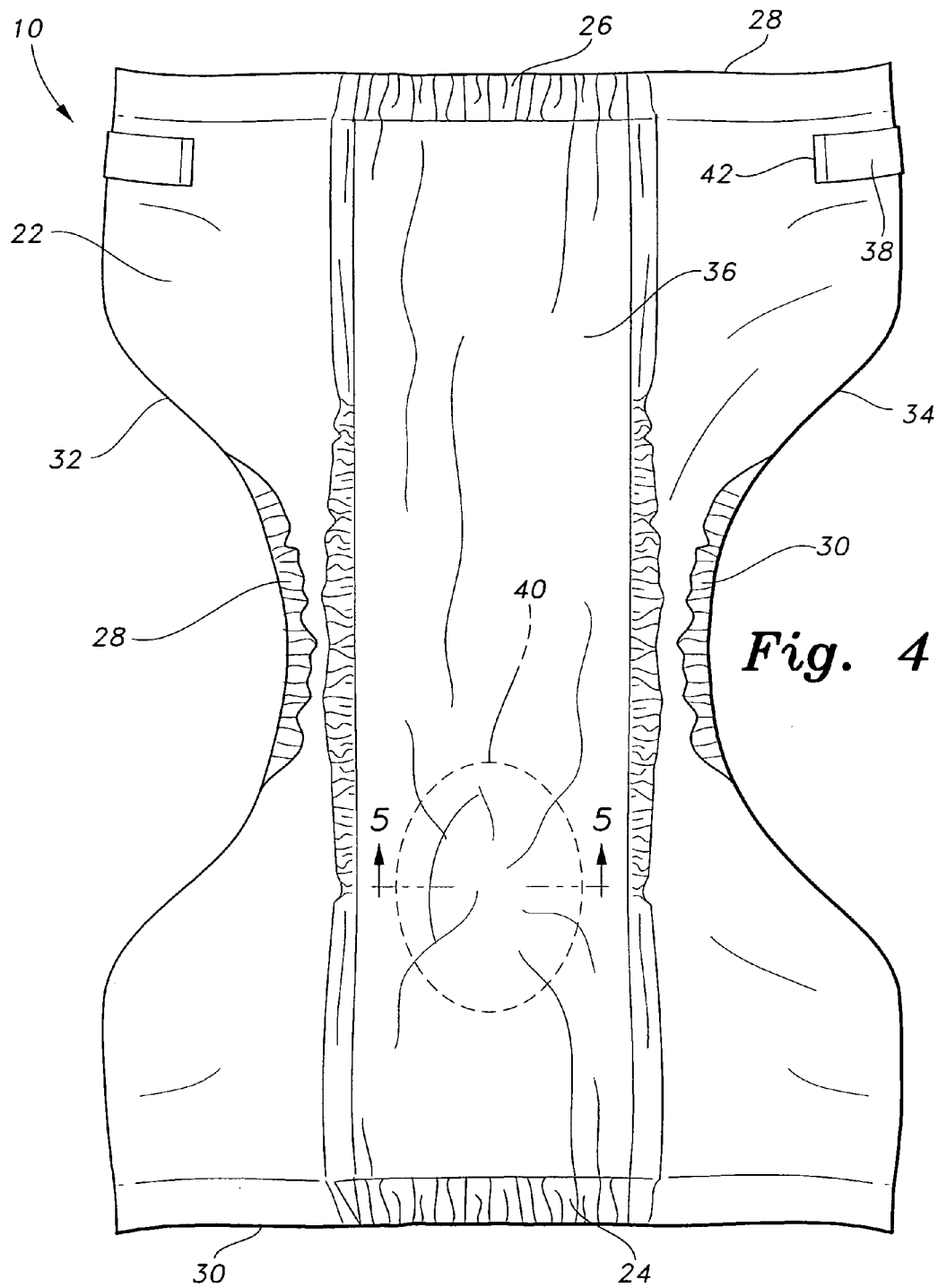
FIG. 4 is a top, plan view of the post circumcision diaper, the protective cup being shown in phantom.

As shown in FIG. 3, the diaper 10 has an outer surface 20 that is constructed of a fluid-impervious material to prevent moisture from seeping out of the diaper and an inner surface 22 that is constructed of an absorbent material to absorb bodily discharge from a baby. When laid flat, as shown in FIG. 4, the diaper 10 has a substantially hourglass shape with substantially straight ends 28 and 30 corresponding to the waist and arcuate sides 32 and 34 corresponding to the sides and leg openings. An elastic waistband 24 and 26 extends across each end 28 and 30 and elastic leg bands 27 and 29 extend along the middle portion of each side 32 and 34. Two strips of adhesive tape 38 are secured to the outer surface 20 with each adhesive strip 38 folding over a side 32 or 34 of the diaper 10 such that a portion of the adhesive strip 38 is secured to a non-sticking area 42 disposed on the inner surface 22. A substantially rectangular portion of the inner surface 22 is reinforced with an extra layer 36 of absorbent material, and a substantially dome-shaped protective cup 40 is disposed between the inner 22 and outer surfaces 20 of the diaper 10.

Figure 2:
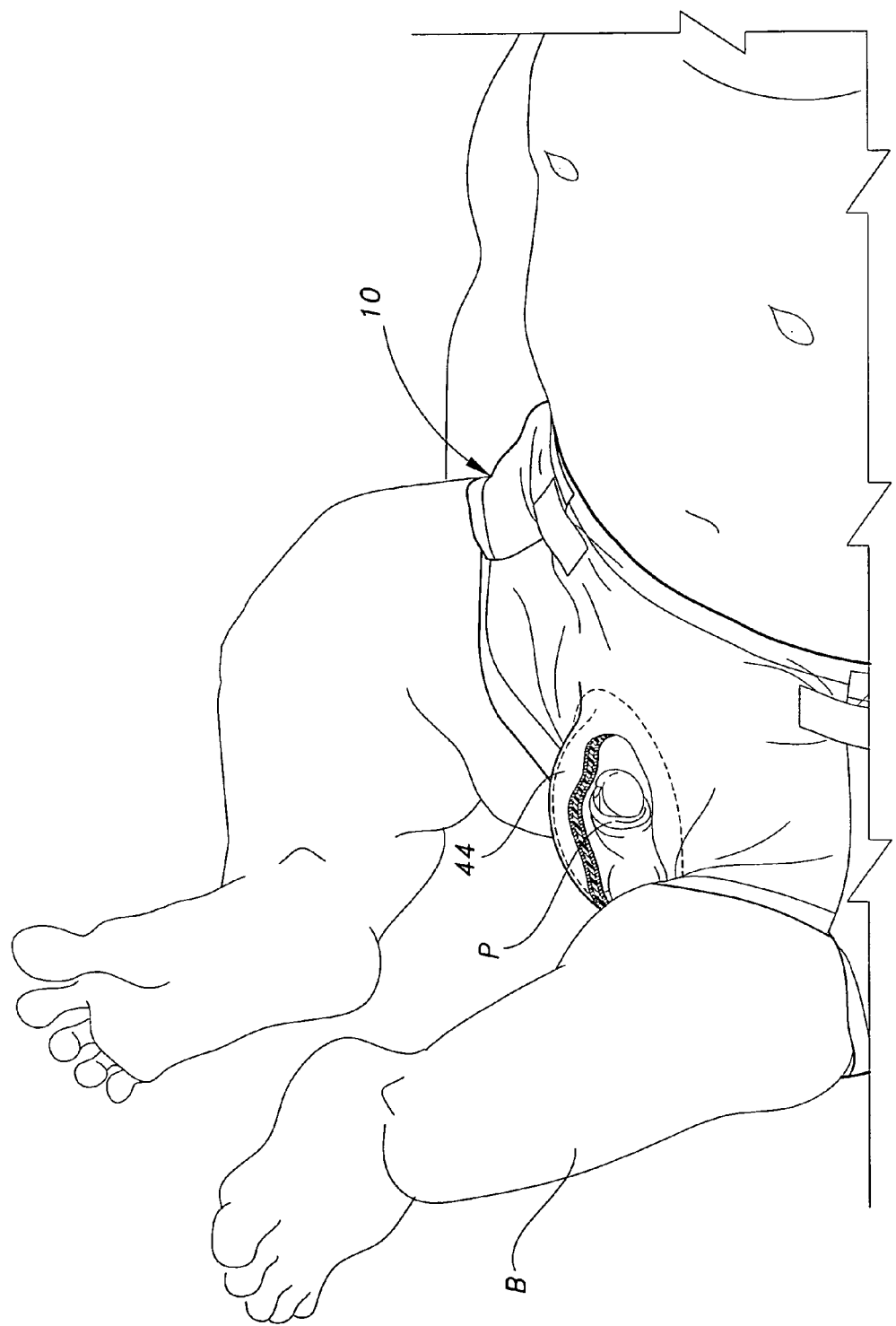
FIG. 2 is an environmental, perspective view of the post circumcision diaper, partly broken away and in section to show the protective cup.

The area 44 of the diaper 10 in which the protective cup 40 is situated between the inner 22 and outer surfaces 20 is convex outward and concave inward as shown in FIGS. 1 and 3. When a baby boy B wears the diaper 10, as shown in FIGS. 1 and 2, the protective cup 40 is positioned over the baby's B penis and scrotum P, the relatively rigid, concave interior of the cup 40 thereby protecting the penis and scrotum P against both direct pressure from the diaper 10 and incidental pressure from persons holding the baby B.

Figure 5:
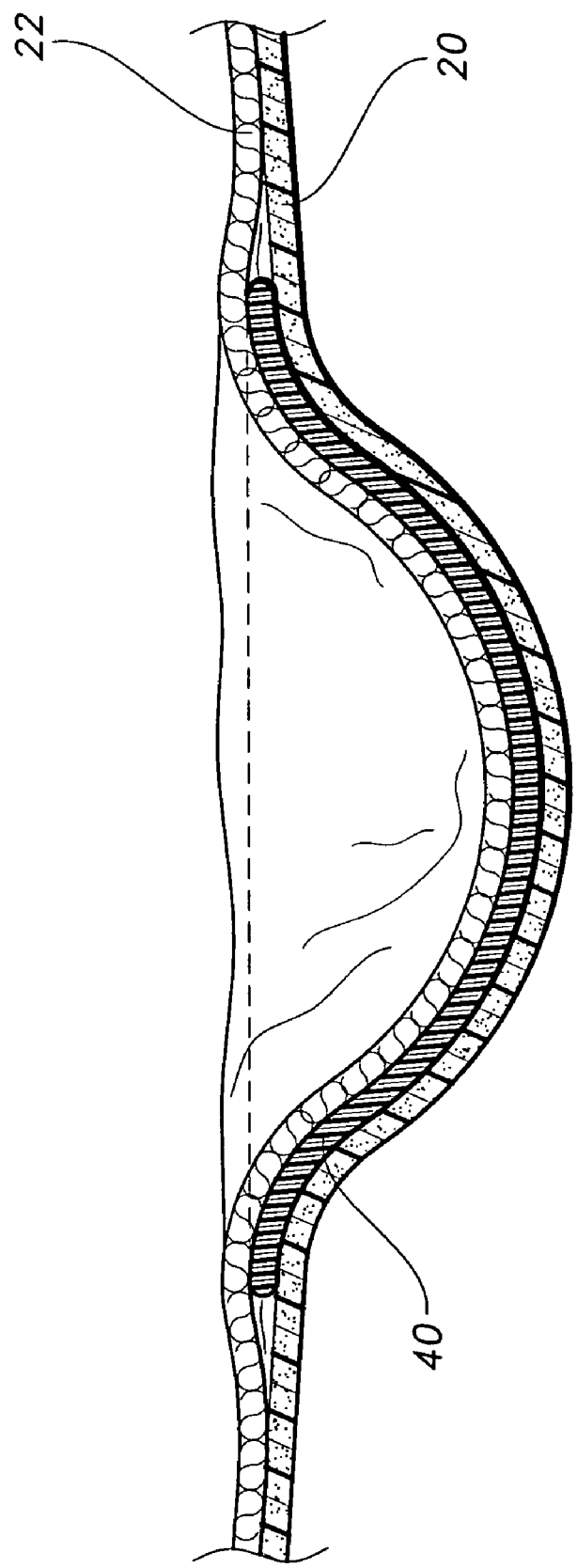
FIG. 5 is a sectional view taken along lines 5—5 of FIG. 4.

The protective cup 40 is constructed of plastic and can be held in position between the inner 22 and outer surfaces 20, as shown in FIG. 5, either by being sewn into the diaper 10 or by an adhesive. The protective cup 40 can be solid or can be perforated to allow for the use of moisture indicators on the outer surface 20 to visibly reflect when the baby has urinated by changing colors, and to fully use the absorptive capacity of the diaper by allowing the baby's urine to pass through the cup. Additionally, the inner surface of the protective cup 40 can be lined with extra absorbent material to provide for additional absorption of urine and thereby keep the surgical area as dry as possible.

Figure 6:
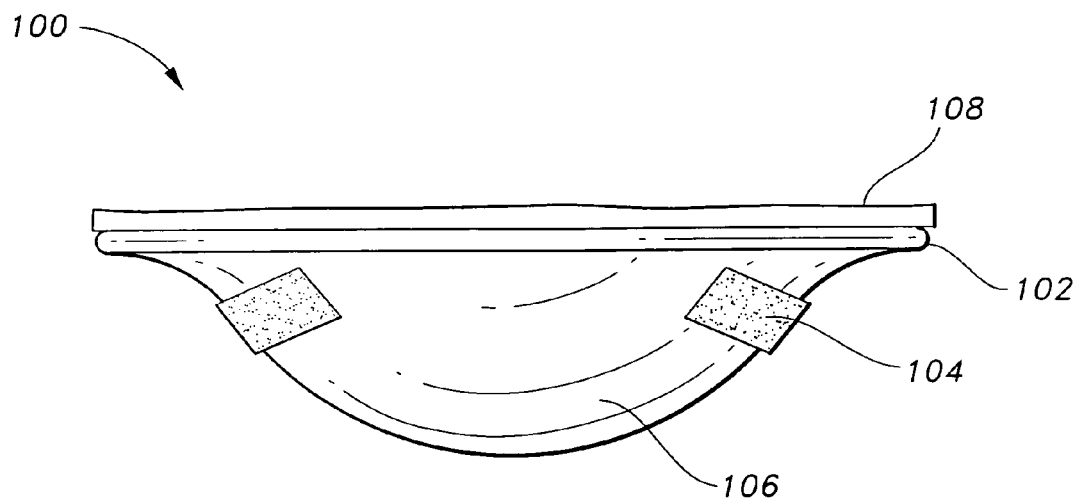
FIG. 6 is an edge view of an alternative embodiment of a post circumcision diaper cup according to the present invention.
Figure 7:
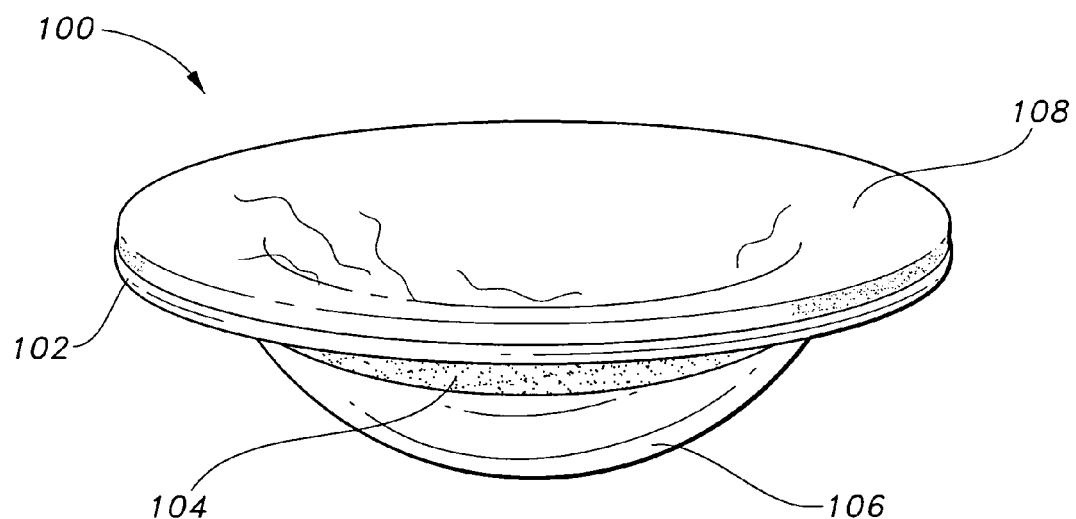
FIG. 7 is a perspective view of the cup of FIG. 6.

In an alternative embodiment, shown in FIGS. 6 and 7, the post circumcision diaper is formed by a protective cup 102 that is configured for aftermarket attachment to the inside of a commercially available disposable diaper (not shown). In this embodiment, the protective cup 102 has adhesive 104 on its outer surface 106 and a layer of soft absorbent material 108 on its inner surface. By pressing outer surface 106 against the inner surface of a commercially available disposable or cloth diaper, the protective cup 102 can be positioned in the diaper such that it protects a baby boy's penis from direct and incidental pressure.

By protecting a baby boy's recently circumcised penis from direct and incidental pressure, both of the embodiments described above help prevent rubbing and irritation of the surgical site, and thereby helps prevent infections that can lead to complications requiring further surgery or an imperfect cosmetic appearance.

It is to be understood that the present invention is not limited to the embodiments described above, but encompasses any and all embodiments within the scope of the following claims.

I claim:

1. A post circumcision diaper, comprising:
    a diaper having an inner and outer surface; and
    a protective cup constructed of a porous material;
    said protective cup having a concave inner surface and a convex outer surface;
    said protective cup being integrated into said diaper with said convex outer surface of said protective cup oriented toward said outer surface of said diaper;
    whereby, when said diaper is worn by a post circumcision baby, said protective cup is positioned over the baby's penis such that said diaper does not lay directly on the penis and such that the penis is protected from external pressure when the baby is being held.

2. The post circumcision diaper according to claim 1, wherein said protective cup is disposed between said inner and said outer surfaces of said diaper.

3. The post circumcision diaper according to claim 1, wherein said protective cup is perforated.

4. The post circumcision diaper according to claim 1, wherein said protective cup is lined with absorbent material.

5. The post circumcision diaper according to claim 1, wherein said protective cup is secured to said diaper by adhesive material.

6. The post circumcision diaper according to claim 1, further comprising moisture indicators disposed on said outer surface of said diaper, whereby said moisture indicators change color when moisture is present.

7. A post circumcision diaper, comprising:
    a diaper having an inner and outer surface; and
    a protective cup having a concave inner surface and a convex outer surface;
    said protective cup being integrated into said diaper with said convex outer surface of said protective cup oriented toward said outer surface of said diaper;
    whereby, when said diaper is worn by a post circumcision baby, said protective cup is positioned over the baby's penis such that said diaper does not lay directly on the penis and such that the penis is protected from external pressure when the baby is being held;
    wherein said protective cup is sewn into said diaper.

8. The post circumcision diaper according to claim 7, wherein said protective cup is made of plastic.

9. A post-circumcision cup for use with a diaper, comprising:
    a protective cup having a concave inner surface and a convex outer surface;
    a layer of absorbent material disposed on said inner surface of said protective cup; and
    adhesive disposed on said outer surface of said protective cup;
    whereby, when said outer surface of said protective cup is pressed against the front inner surface of a diaper, a post circumcision diaper is formed, said protective cup being disposed over and protecting the penis of a recently circumcised baby boy wearing said post circumcision diaper.

10. The cup according to claim 9, wherein said protective cup is constructed of plastic.

11. The cup according to claim 9, wherein said protective cup is perforated.

12. The cup according to claim 9, wherein said protective cup is constructed of a porous material.

* * * * *